(12) United States Patent
Callahan et al.

(10) Patent No.: US 7,300,952 B2
(45) Date of Patent: Nov. 27, 2007

(54) NF-κB INHIBITORS

(75) Inventors: James F. Callahan, King of Prussia, PA (US); Zehong Wan, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 528 days.

(21) Appl. No.: 10/517,111

(22) PCT Filed: May 29, 2003

(86) PCT No.: PCT/US03/16876

§ 371 (c)(1),
(2), (4) Date: Dec. 3, 2004

(87) PCT Pub. No.: WO03/104219

PCT Pub. Date: Dec. 18, 2003

(65) Prior Publication Data

US 2006/0058371 A1    Mar. 16, 2006

Related U.S. Application Data

(60) Provisional application No. 60/386,557, filed on Jun. 6, 2002.

(51) Int. Cl.
*A61K 31/381* (2006.01)
*C07D 333/52* (2006.01)

(52) U.S. Cl. .......... 514/447; 549/29; 549/41; 549/49; 549/57; 514/438; 514/443

(58) Field of Classification Search .......... 549/29, 549/41, 49, 57; 514/438, 443, 447
See application file for complete search history.

(56) References Cited

U.S. PATENT DOCUMENTS

| 4,782,080 A | 11/1988 | Witzel |
| 6,018,056 A | 1/2000 | Schmid et al. |

FOREIGN PATENT DOCUMENTS

| EP | 0 747 052 | 12/1996 |
| WO | WO 02/30353 | 4/2002 |

OTHER PUBLICATIONS

Modica et al., "[[(Arylpiperazinyl)alkyl]thio]thieno[2,3-d]pyrimidinone Derivatives as High Affinity, Selective 5-HT$_{1A}$ Receptor Ligands". *J. Med. Chem.*, 40: 574-585 (1997).
Gewald et al., "2-Amino-thionaphthene". *Chemische Berichte*, 101: 1933-1939 (1968).

*Primary Examiner*—Golam M. M. Shameem
(74) *Attorney, Agent, or Firm*—John L. Lemanowicz; Laura K. Madden

(57) ABSTRACT

The present invention provides novel compounds and methods for using them to treat diseases with aminothiophene inhibitors of IKK-β phosphorylation of IκB. In so doing these aminothiophene inhibitors block pathological activation of transcription factor NF-κB in which diseases excessive activation of NF-κB is implicated.

2 Claims, No Drawings

NF-κB INHIBITORS

This application is a 371 of International Application No. PCT/US03/16876, filed May 29, 2003, which claims the benefit of U.S. Provisional Application No. 60/386,557, filed Jun. 6, 2002.

FIELD OF THE INVENTION

This invention relates in general to a method of inhibiting pathological activation of the transcription factor NF-κB (nuclear factor-κB) using amino-benzothiophene compounds. Such methods are particularly useful for treating diseases in which activation of NF-κB is implicated. More specifically, these methods may be used for inhibiting IKK-β (IκB kinase-β, also known as IKK-2) phosphorylation of IκB (inhibitory protein κB)—which prevents subsequent degradation and activation of NF-κB dimers. Such methods are useful in the treatment of a variety of diseases associated with NF-κB activation including inflammatory and tissue repair disorders; particularly rheumatoid arthritis, inflammatory bowel disease, asthma and COPD (chronic obstructive pulmonary disease) osteoarthritis; osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, Ataxia Telangiestasia.

BACKGROUND OF THE INVENTION

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoregualtory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427-433 and Aupperle et al. *J. Immunology* 2001; 166:2705-11. More recently, the intra-articular administration of a wild type IKK-β adenoviral construct was shown to cause paw swelling while intra-articular administration of dominant-negative IKK-β inhibited adjuvant-induced arthritis in rat. See Tak et al. *Arthritis and Rheumatism* 2001; 44:1897-1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported, strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytoline-induced muscle wasting (Guttridge et al. *Science;* 2000; 289: 2363-2365.) further supporting the potential of NF-κB inhibitors as novel cancer therapies.

Several NF-κB inhibitors are described in C. Wahl, et al. *J. Clin. Invest.* 101(5), 1163-1174 (1998), R. W. Sullivan, et al. *J. Med. Chem.* 41, 413-419 (1998), J. W. Pierce, et al. *J. Biol. Chem.* 272, 21096-21103 (1997)

The marine natural product hymenialdisine is known to inhibit NF-κB. Roshak, A., et al., *JPET,* 283, 955-961 (1997). Breton, J. J and Chabot-Fletcher, M. C., *JPET,* 282, 459-466 (1997).

Additionally, patent applications have been filed on aminothiophene inhibitors of the IKK-2, see Callahan, et al., WO 2002030353; Baxter, et al., WO 2001058890, Faull, et al., WO 2003010158; Griffiths, et al., WO2003010163; Fancelli, et al., WO 200198290; imidazole inhibitors of IKK-2, see Callahan, et al., WO 200230423; anilinophenylpyrimidine inhibitors of IKK-2, see Kois, et al., WO 2002046171; β-carboline inhbitors of IKK-2, see Ritzeler, et al., WO 2001068648, Ritzeler, et al., EP 1134221; Nielsch, et al. DE 19807993; Ritzeler, et al., EP 1209158; indole inhbitors of IKK-2, see Ritzeler, et al., WO 2001030774; benzimidazole inhibitors of the IKK-2, see Ritzeler, et al., DE 19928424; Ritzeler et al, WO 2001000610; aminopyridine inhibitors of IKK-2, see Lowinger, et al, WO2002024679; Murata, et al, WO 2002024693; Murata, et al., WO2002044153;pyrazolaquinazoline inhibitors of IKK-2, see Beaulieu, et al., WO2002028860; Burke et al, WO2002060386, Burke, et al. U.S. 20030022898; quinoline inhibitors of IKK-2, Browner, et al., WO2002041843, Browner, et al., U.S. 20020161004 and pyridylcyanoguanidine inhibitors of IKK-2, see Bjorkling, et al., WO 2002094813, Binderup et al, WO 2002094322 and Madsen, et al., WO 200294265. The natural products staurosporine, quercetin, K252a and K252b have been shown to be IKK-2 inhibitors, see Peet, G. W. and Li, J. J. *Biol. Chem.,* 274, 32655-32661 (1999) and Wisniewski, D., et al., *Analytical Biochem.* 274, 220-228 (1999). Synthetic inhibitors of IKK-2 have also been described, see Burke, et al. *J. Biol. Chem.,* 278, 1450-1456 (2003) and Murata, et al., *Bioorg. Med. Chem. Lett.,* 13, 913-198 (2003) have described IKK-2 inhibitors.

U.S. Pat. No. 3,963,750 describes the preparation of certain aminothiophenes.

SUMMARY OF THE INVENTION

The present invention involves novel compounds and novel methods of inhibiting the activation transcription factor NF-κB using the present compounds.

An object of the present invention is to provide a method for treating diseases which may be therapeutically modified by altering the activity of transcription factor NF-κB.

Accordingly, in the first aspect, this invention provides a pharmaceutical composition comprising a compound according to Formula I.

In another aspect, this invention provides a method of treating diseases in which the disease pathology may be therapeutically modified by inhibiting phosphorylation and subsequent degradation of IκB by IKK-β.

In still another aspect, this invention provides a method of treating diseases in which the disease pathology may be therapeutically modified by inhibiting pathological activation of NF-κB.

In a particular aspect, this invention provides methods for treating a variety of diseases associated with NF-κB activation including inflammatory and tissue repair disorders, particularly rheumatoid arthritis, inflammatory bowel disease, asthma and COPD (chronic obstructive pulmonary disease) osteoarthritis, osteoporosis and fibrotic diseases, dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome and Ataxia Telangiestasia

DETAILED DESCRIPTION OF THE INVENTION

The compounds of the present invention are selected from Formula (I) herein below:

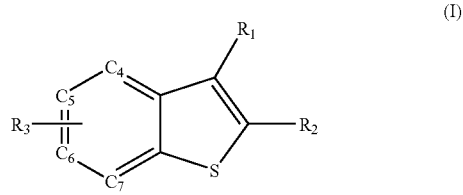

$R_1$ represents $CONH_2$;
$R_2$ represents $NR_4R_5$;
$R_3$ is selected from the group consisting of H, CN, $CF_3$, halogen, aryl, heteroaryl, alkyl, O-alkyl, and S-alkyl; and can be attached to either $C_4$, $C_5$, $C_6$ or $C_7$;
$R_4$ represents H or alkyl; and
$R_5$ is selected from the group consisting of H, CO-alkyl, $SO_2$-alkyl, $CONH_2$, CONH-alkyl, CONH-aryl, CONH-heteroaryl, $CSNH_2$, CSNH-alkyl, CSNH-aryl, CSNH-heteroaryl, $SO_2NH_2$, $SO_2NH$-alkyl, $SO_2NH$-aryl, and $SO_2NH$-heteroaryl; or a pharmaceutically acceptable salt thereof.

Preferred compounds useful in the present invention include:
2-Amino-6-(4-fluoro-phenyl)-benzo[b]thiophene-3-carboxylic acid amide; and
2-Ureido-benzo[b]thiophene-3-carboxylic acid amide.

This invention provides methods for treating a variety of diseases associated with NF-κB activation including inflammatory and tissue repair disorders; particularly rheumatoid arthritis, inflammatory bowel disease, asthma and COPD (chronic obstructive pulmonary disease) osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome, and Ataxia Telangiestasia.

DEFINITIONS

The present invention includes all hydrates, solvates, complexes and prodrugs of the compounds of this invention. Prodrugs are any covalently bonded compounds, which release the active parent, drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

As used herein, "alkyl" refers to an optionally substituted hydrocarbon group joined by single carbon-carbon bonds and having 1-6 carbon atoms joined together. The alkyl hydrocarbon group may be linear, branched or cyclic, saturated or unsaturated. Substituents on optionally substituted alkyl are selected from the group consisting of aryl, OH, O-alkyl, CO, halogen, $CF_3$, and $OCF_3$.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Substituents are selected from the group consisting of halogen, $C_{1-4}$ alkyl, $NH_2$, $OCF_3$, $CF_3$, O-alkyl, S-alkyl, CN, CHO, $SO_2$-alkyl and $NO_2$.

As used herein, "heteroaryl" refers to an optionally substituted aromatic group with at least one ring having a conjugated pi-electron system, containing up to two conjugated or fused ring systems and 1-3 heteroatoms selected from O, S and N. Heteroaryl includes carbocyclic heteroaryllaryl, aryl-heteroaryl and biheteroarylaryl groups, all of which may be optionally substituted. Preferred aryl include phenyl and naphthyl. More preferred aryl include phenyl. Preferred substituents are selected from the group consisting of halogen, $C_{1-4}$ alkyl, $NH_2$, $OCF_3$, $CF_3$, O-alkyl, S-alkyl, CN, CHO, $SO_2$-alkyl and $NO_2$. Examples of heteroaryl rings included pyrrole, furan, thiophene, indole, isoindole, benzofuran, isobenzofuran, benzothiphene, pyridine, quinoline, isoquinoline, quinolizine, pyrazole, imidazole, isoxazole, oxazole, isothiazole, thiazole, pyridazine, pyrimidine, and pyrazine.

As used herein "halogen" refers to include F, Cl, Br, and I.

METHODS OF PREPARATION

The following methods and examples are intended to be illustrative of the present invention but not limiting in any way.

The general preparation of analogs of 2-aminobenzothiophene-3-carboxylic acid amide is shown in Scheme I.

The synthesis starts with commercially available ethyl 2-amino-4,5,6,7-tetrahydrobenzothiophene-3-carboxylate (1). Protection of the amino group with acetyl chloride (AcCl) and oxidation with 2,3-dichloro-5,6-dicyano-1,4-benzoquinone (DDQ) provide benzothiophene 3. Deprotection of the acetamide followed by bromination with N-bromosuccinimide (NBS) furnish 2-aminobenzothiophene 5. Palladium(0) mediated Suzuki cross-coupling with boronic acid/ester then afford 6. Reprotection of the amino group with di-tert-butyl dicarbonate [$(Boc)_2O$] and hydrolysis of the ester group produce acid 8. The resultant acid is activated with 1,1'-carbonyldiimidazole (CDI), followed by reaction with ammonium hydroxide and treatment with trifluoroacetic acid (TFA) then furnish 2-amino-benzothiophene-3-carboxylic amide 10. Compound 10 can be readily transformed to primary urea 11 by reaction with chlorosulfonyl isocyanate or to substituted urea 12 by isocyantes (Scheme II).

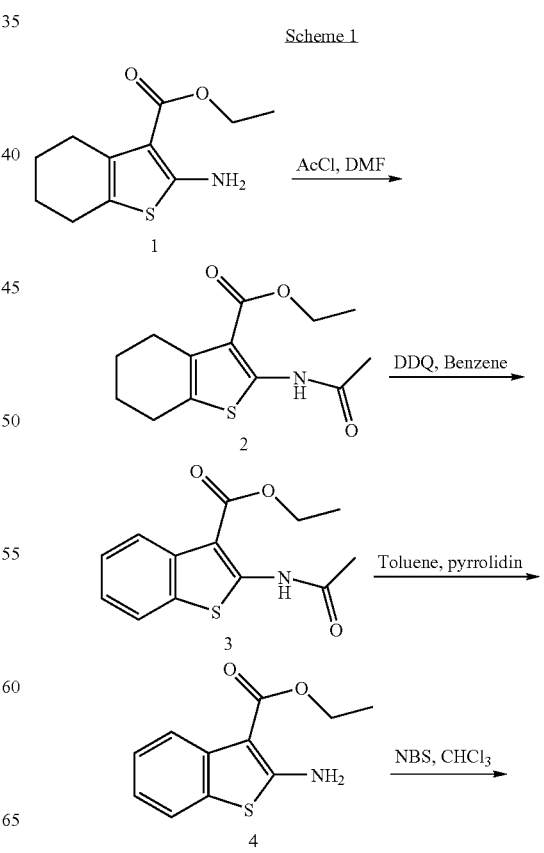

Scheme 1

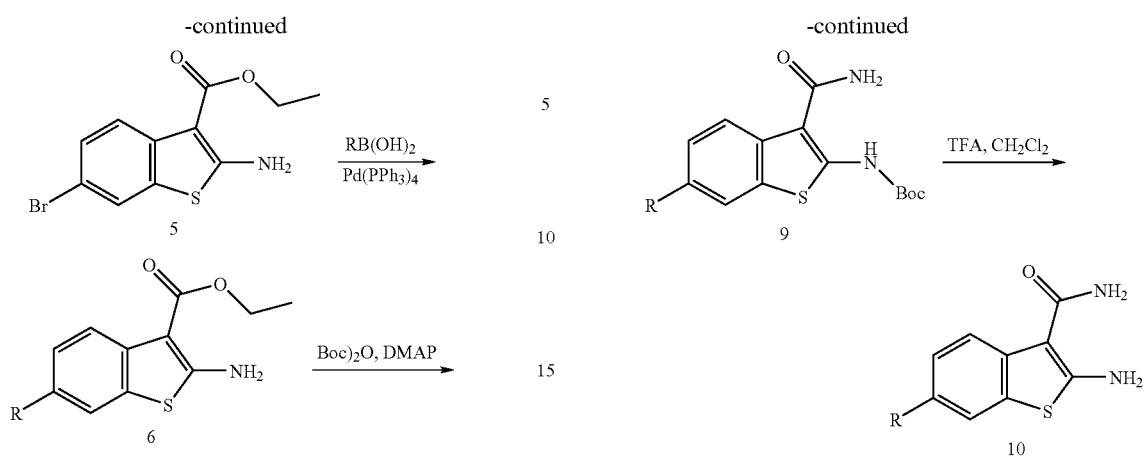
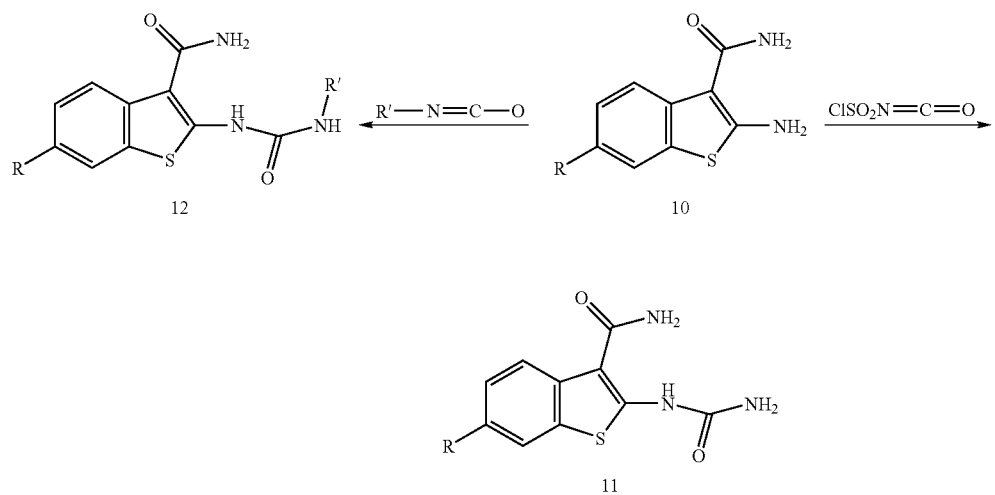
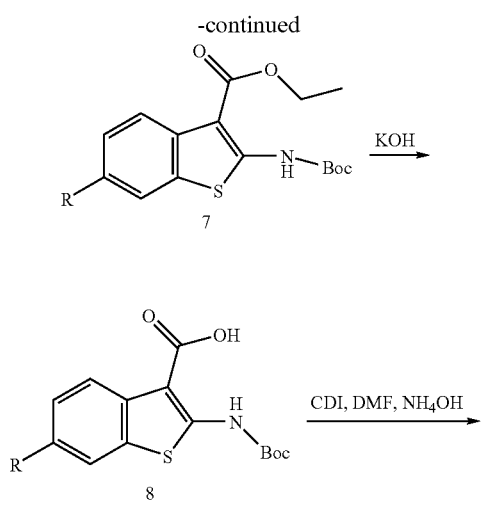
Urea 15 is synthesized from 2-amino-benzo[b]thiophene-3-carbonitrile (13, Scheme III) employing a two-step procedure; nitrile hydrolysis followed by urea formation.
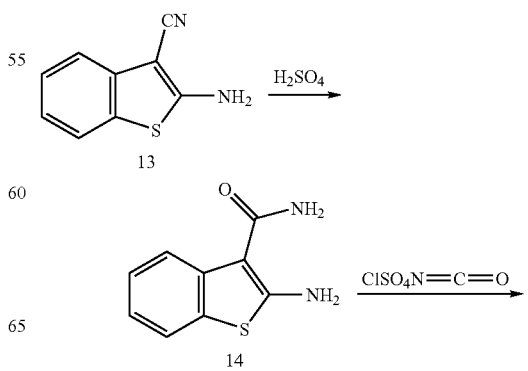

-continued

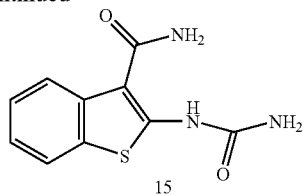

The following examples are intended to be illustrative of the present invention but not limiting in anyway.

EXAMPLES AND EXPERIMENTAL

General

Nuclear magnetic resonance spectra were recorded at either 250, 300 or 400 MHz using, respectively, a Bruker AM 250, Bruker ARX 300 or Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers (cm$^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel.

Where indicated, certain of the materials were purchased from the Aldrich Chemical Co., Milwaukee, Wis., TCI America, Portland, Oreg.

Example 1

Preparation of 2-amino-6-(4-fluoro-phenyl)-benzo[b]thiophene-3-carboxylic Acid Amide 1a) 2-Acetylamino-4, 5, 6, 7-tetrahydrobenzothiophene-3-carboxylic Acid Ethyl Ester To a solution of ethyl 2-amino-4, 5, 6, 7-tetrahydrobenzothiophene-3-carboxylate (16 g, 71.1 mmol) in THF (100 mL) was added 4-(dimethylamino)pyridine (434 mg, 3.55 mmol) and acetyl chloride (6.1 mL, 85.3 mmol). After stirring for 2 h at room temperature, the solution was diluted with brine solution (500 mL) and extracted with ethyl acetate (500 mL, 3×). The combined organic phases were dried over MgSO$_4$, filtered, and concentrated to provide the title compound (18.3 g, 96%) as a light yellow solid: MS (ES) m/z 268 (M+H)$^+$.

1b) 2-Acetylamino-benzo[b]thiophene-3-carboxylic Acid Ethyl Ester

A solution of 1a (3.0 g, 11.24 mmol) in benzene (100 mL) was mixed with 2,3-dichloro-5,6-dicyano-1,4-benzoquinone (3.8 g, 16.85 mmol). The resultant mixture was heated at reflux for 2 h, diluted with saturated NaHCO$_3$ solution (300 mL) and extracted with ethyl acetate (300 mL, 3×). The combined organic phases were dried over MgSO$_4$, filtered, and concentrated. Flash chromatography (hexanes/ethyl acetate, 8:1) then provided the title compound (1.06 g, 35%) as a yellow solid: MS (ES) m/z 264 (M+H)$^+$;

1c) 2-Amino-benzo[b]thiophene-3-carboxylic Acid Ethyl Ester

To a solution of 1b (1.06 g, 4.03 mmol) in toluene (100 mL) was added pyrrolidine (5 mL). The resultant mixture was heated at 100° C. for 8 h, diluted with brine solution (200 mL) and extracted with ethyl ether (300 mL, 3×). The combined organic phases were dried over MgSO$_4$, filtered, and concentrated. Flash chromatography (hexanes/ethyl acetate, 4:1) then afforded the title compound (0.76 g, 85%) as a yellow solid: MS (ES) m/z 222 (M+H)$^+$; $^1$H NMR (400 MHz, CDCl$_3$) δ8.14 (d, J=8.0 Hz, 1H), 7.53 (d, J=7.2 Hz, 1H), 7.28 (m, 1H), 7.04 (m, 1H), 6.51 (brs, 2H), 4.45 (q, J=7.2 Hz, 2H), 1.50 (t, J=7.2 Hz, 3H).

1d) 2-Amino-6-bromo-benzo[b]thiophene-3-carboxylic Acid Ethyl Ester

To a solution of 1c (760 mg, 3.44 mmol) in CHCl$_3$ (10 mL) was added N-bromosuccinimide (673 mg, 3.78 mmol). The resultant mixture was stirred for 1 h, then mixed with saturated NaHCO$_3$ solution (100 mL), and extracted with methylene chloride (100 mL, 3×). The combined organic phases were dried over MgSO$_4$, filtered, and concentrated. Flash chromatography (hexanes/ethyl acetate, 4:1) then provided the title compound (930 mg, 90%) as a yellow solid: MS (ES) m/z 300 (M+H)$^+$; $^1$H NMR (400 MHz, CDCl$_3$) δ7.96 (d, J=8.8 Hz, 1H), 7.63 (s, 1H), 7.42 (d, J=8.8 Hz, 1H), 6.52 (brs, 2H), 4.42 (q, J=7.2 Hz, 2H), 1.48 (t, J=7.2 Hz, 3H).

1e) 2-Amino-6-(4-fluoro-phenyl)-benzo[b]thiophene-3-carboxylic Acid Ethyl Ester

To a solution of 1d (200 mg, 0.67 mmol) in 1,4-dioxane/water (40 mL, 3:1) was added 4-fluorophenylboronic acid (209 mg, 1.34 mmol), NaHCO$_3$ (225 mg, 2.68 mmol) and Pd(PPh$_3$)$_4$ (9% Pd, 79 mg, 0.067 mmol). The resultant mixture was heated at 110° C. for 1 h, diluted with brine solution (50 mL) and extracted with ethyl acetate (50 mL, 3×). The combined organic phases were dried over MgSO$_4$, filtered, and concentrated. Flash chromatography (hexanes/ethyl acetate, 4:1) then provided the title compound (190 mg, 90%) as a pink sticky oil: MS (ES) m/z 316 (M+H)$^+$; $^1$H NMR (400 MHz, CDCl$_3$) δ8.16 (d, J=8.4 Hz, 1H), 7.69 (s, 1H), 7.62 (m, 2H), 7.50 (d, J=8.4 Hz, 1H), 7.15 (m, 2H), 6.58 (brs, 2H), 4.46 (q, J=7.2 Hz, 2H), 1.50 (t, J=7.2 Hz, 3H).

1f) 2-tert-Butoxycarbonylamino-6-(4-fluoro-phenyl)-benzo[b]thiophene-3-carboxylic Acid Ethyl Ester To a solution of 1e (190 mg, 0.603 mmol) in THF (10 mL) was added 4-(dimethylamino)pyridine (7.4 mg, 0.06 mmol) and di-tert-butyl dicarbonate (158 mg, 0.724 mmol). The resultant mixture was stirred at room temperature for 1 h, diluted with brine solution (50 mL), and extracted with ethyl acetate (50 mL, 3×). The combined organic phases were dried over MgSO$_4$, filtered, and concentrated. Flash chromatography (hexanes/ethyl acetate, 4:1) then provided the title compound (200 mg, 80%) as a yellow solid: MS (ES) m/z 416 (M+H)$^+$.

1g) 2-tert-Butoxycarbonylamino-6-(4-fluoro-phenyl)-benzo[b]thiophene-3-carboxylic Acid A solution of 1f (80 mg, 0.193 mmol) in ethanol/water (1:1, 10 mL) was mixed with KOH (21.6 mg, 0.39 mmol). The resultant mixture was heated at 60° C. for 1 h, diluted with HCl (30 mL, 1N), and extracted with ethyl acetate (30 mL, 3×). The combined organic phases were dried over $MgSO_4$, filtered, and concentrated to afford the title compound (62 mg, 84%) as a white solid: MS (ES) m/z 388 $(M+H)^+$.

1h) [3-Carbamoyl-6-(4-fluoro-phenyl)-benzo[b]thiophene-2-yl]-carbamic Acid Tert-butyl Ester To a solution of 1g (150 mg, 0.38 mmol) in DMF (3 mL) was added 1,1'-carbonyl diimidazole (125 mg, 0.78 mmol). The resultant solution was stirred at room temperature for 1 h and mixed with ammonium hydroxide (37%, 5 mL). The mixture was diluted with brine solution (10 mL) and extracted with ethyl acetate (20 mL, 3×). The combined organic phases were dried over $MgSO_4$, filtered, and concentrated. Flash chromatography (hexanes/ethyl acetate, 1:1) then provided the title compound (48 mg, 32%) as a white solid: MS (ES) m/z 387 $(M+H)^+$; $^1H$ NMR (400 MHz, $CDCl_3$) δ11.14 (s, 1H), 7.94 (s, 1H), 7.85 (d, J=4.4 Hz, 1H), 7.61 (m, 3H), 7.18 (m, 2H), 5.87 (brs, 2H), 1.59 (s, 9H).

1i) 2-Amino-6-(4-fluoro-phenyl)-benzo[b]thiophene-3-carboxylic Acid Amide

A solution of 1h (20 mg, 0.051 mmol) in $CH_2Cl_2$ (5 mL) was mixed with trifluoroacetic acid (0.5 mL). The resultant solution was stirred at room temperature for 1 h, then mixed with saturated $NaHCO_3$ solution (30 mL), and extracted with ethyl acetate (30 mL, 3×). The combined organic phases were dried over $MgSO_4$, filtered, and concentrated. Flash chromatography (hexanes/ethyl acetate, 1:1) provided the title compound (8 mg, 55%) as a white solid: MS (ES) m/z 287 $(M+H)^+$; $^1H$ NMR (400 MHz, $CD_3OD$) δ7.73 (s, 1H), 7.63-7.50 (m, 3H), 7.42 (m, 1H), 7.08 (m, 2H).

Example 2

Preparation of
2-ureido-benzo[b]thiophene-3-carboxylic Acid Amide 2a) 2-Amino-benzo[b]thiophene-3-carboxylic Acid Amide A solution of 2-amino-benzo[b]thiophene-3-carbonitrile (50 mg, 0.29 mmol) in concentrated $H_2SO_4$ (1.5 mL) was heated at 60° C. for 2 h. The solution was poured into ice-water (5 mL), mixed with saturated $NaHCO_3$ solution (30 mL), and extracted with ethyl acetate (30 mL, 3×). The combined organic phases were dried over $MgSO_4$, filtered, and concentrated. Flash chromatography (hexanes/ethyl acetate, 1:1) then provided the title compound (23 mg, 41%) as a white solid: MS (ES) m/z 193 $(M+H)^+$.

2b) 2-Ureido-benzo[b]thiophene-3-carboxylic Acid Amide

To the mixture of 2a (20 mg, 0.104 mmol) in $CH_2Cl_2$ (10 mL) was added chlorosulfonyl isocyanate (15 μL, 0.15 mmol). The resultant mixture was stirred at room temperature for 1 h and mixed with water (0.5 mL). Separation via a reverse phase HPLC provided the title compound (10 mg, 40%) as a white solid: MS (ES) m/z 236 $(M+H)^+$; $^1H$ NMR (400 MHz, DMSO-$d_6$) δ10.77 (s, 1H), 7.84 (m, 2H), 7.56 (brs, 3H), 7.20 (m, 1H), 7.08 (m, 1H), 6.98 (brs, 1H).

This invention provides a pharmaceutical composition, which comprises a compound according to Formula, I and a pharmaceutically acceptable carrier, diluent or excipient.

Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Typical compositions for inhalation are in the form of a dry powder, solution, suspension or emulsion. Administration may for example be by dry powder inhaler (such as unit dose or multi-dose inhaler, e.g. as described in U.S. Pat. No. 5,590,645 or by nebulisation or in the form of a pressurized aerosol. Dry powder compositions typically employ a carrier such as lactose, trehalose or starch. Compositions for nebulisation typically employ water as vehicle. Pressurized aerosols typically employ a propellant such as dichlorodifluoromethane, trichlorofluoromethane or, more preferably, 1,1,1,2-tetrafluoroethane, 1,1,1,2,3,3,3-heptafluoro-n-propane or mixtures thereof. Pressurized aerosol formulations may be in the form of a solution (perhaps employing a solubilising agent such as ethanol) or a suspension which may be excipient free or employ excipients including surfactants and/or co-solvents (e.g. ethanol). In dry powder compositions and suspension aerosol compositions the active ingredient will preferably be of a size suitable for inhalation (typically having mass median diameter (MMD) less than 20 microns e.g. 1-10 especially 1-5 microns). Size reduction of the active ingredient may be necessary e.g. by micronisation.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

For rectal administration, the compounds of this invention may also be combined with excipients such as cocoa butter, glycerin, gelatin or polyethylene glycols and molded into a suppository.

The methods of the present invention include topical inhaled and intracolonic administration of the compounds of Formula I. By topical administration is meant non-systemic administration, including the application of a compound of the invention externally to the epidermis, to the buccal cavity and instillation of such a compound into the ear, eye and nose, wherein the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician While it is possible for an active ingredient to be administered alone as the raw chemical, it is preferable to present it as a pharmaceutical formulation. The active ingredient may comprise, for topical administration, from 0.01 to 5.0 wt %. of the formulation.

The topical formulations of the present invention, both for veterinary and for human medical use, comprise an active ingredient together with one or more acceptable carriers therefor and optionally any other therapeutic ingredients. The carrier must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container, which is then sealed and sterilized by autoclaving, or maintaining at 90-100 C for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap, a mucilage, an oil of natural origin such as almond, corn, arachis, castor or olive oil, wool fat or its derivatives, or a fatty acid such as stearic or oleic acid together with an alcohol such as propylene glycol or macrogols. The formulation may incorporate any suitable surface active agent such as an anionic, cationic or non-ionic surface active agent such as sorbitan esters or polyoxyethylene derivatives thereof. Suspending agents such as natural gums, cellulose derivatives or in organic materials such as silicaceous silicas, and other ingredients such as lanolin, may also be included.

UTILITY OF THE PRESENT INVENTION

The compounds of Formula I are useful as inhibitors of the IKK-beta kinase phosphorylation of IκB and as such are inhibitors of NF-κB activation. The present method utilizes compositions and formulations of said compounds, including pharmaceutical compositions and formulations of said compounds.

The present invention particularly provides methods of treatment of diseases associated with inappropriate NF-κB activation, which methods comprise administering to an animal, particularly a mammal, most particularly a human in need thereof one or more compounds of Formula I. The present invention particularly provides methods for treating inflammatory and tissue repair disorders, particularly rheumatoid arthritis, inflammatory bowel disease, asthma and COPD (chronic obstructive pulmonary disease) osteoarthritis, osteoporosis and fibrotic diseases; dermatosis, including psoriasis, atopic dermatitis and ultraviolet radiation (UV)-induced skin damage, autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome and Ataxia Telangiestasia.

For acute therapy, parenteral administration of one or more compounds of Formula I is useful. An intravenous infusion of the compound in 5% dextrose in water or normal saline, or a similar formulation with suitable excipients, is most effective, although an intramuscular bolus injection is also useful. Typically, the parenteral dose will be about 0.01 to about 50 mg/kg; preferably between 0.1 and 20 mg/kg, in a manner to maintain the concentration of drug in the plasma at a concentration effective to inhibit IKK-beta and therefore activation of NF-κB. The compounds are administered one to four times daily at a level to achieve a total daily dose of about 0.4 to about 80 mg/kg/day. The precise amount of a compound used in the present method which is therapeutically effective, and the route by which such compound is best administered, is readily determined by one of ordinary skill in the art by comparing the blood level of the agent to the concentration required to have a therapeutic effect.

The compounds of Formula I may also be administered orally to the patient, in a manner such that the concentration of drug is sufficient to inhibit IKK-beta and therefore activation of NF-κB or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

The compounds of Formula I may also be administered topically to the patient, in a manner such that the concentration of drug is sufficient to inhibit IKK-beta and therefore activation of NF-κB or to achieve any other therapeutic indication as disclosed herein. Typically, a pharmaceutical composition containing the compound is administered in a topical formulation of between about 0.01% to about 5% w/w.

No unacceptable toxicological effects are expected when compounds of the present invention are administered in accordance with the present invention.

The ability of the compounds described herein to inhibit the activation of NF-κB is clearly evidenced in their ability to inhibit the phosphorylation of the N-terminal fragment of IκB-α (by IKK-β(see Table 1 for examples). These compounds also block the degradation of IκB-α and the nuclear translocation of NF-κB in human monocytes and other mammalian cells upon activation of the cells with a pro-inflammatory stimulii (e.g., TNF-α, LPS, etc.). In addition these compounds inhibit pro-inflammatory mediator production from LPS-stimulated human monocytes and stimulated human primary synovial fibroblasts. The utility of the present NF-κB inhibitors in the therapy of diseases is premised on the importance of NF-κB activation in a variety of diseases.

NF-κB plays a key role in the regulated expression of a large number of pro-inflammatory mediators including cytokines such as TNF, IL-1β, IL-6 and IL-8 (Mukaida et al., 1990; Liberman and Baltimore, 1990; Matsusaka et al., 1993), cell adhesion molecules, such as ICAM and VCAM (Marui et al., 1993; Kawai et al., 1995; Ledebur and Parks, 1995), and inducible nitric oxide synthase (iNOS) (Xie et al., 1994; Adcock et al., 1994). (Full reference citations are at the end of this section). Such mediators are known to play a role in the recruitment of leukocytes at sites of inflammation and in the case of iNOS, may lead to organ destruction in some inflammatory and autoimmune diseases (McCartney-Francis et al., 1993; Kleemann et al., 1993.

Evidence for an important role of NF-κB in inflammatory disorders is obtained in studies of asthmatic patients. Bronchial biopsies taken from mild atopic asthmatics show significant increases in the number of cells in the submucosa staining for activated NF-κB, total NF-κB, and NF-κB-regulated cytokines such as GM-CSF and TNFα compared to biopsies from normal non-atopic controls (Wilson et al., 1998). Furthermore, the percentage of vessels expressing NF-κB immunoreactivity is increased as is IL-8 immunoreactivity in the epithelium of the biopsy specimens (Wilson et al., 1998). As such, inhibition of IL-8 production through the inhibition of NF-κB, as has been demonstrated by these compounds would be predicted be beneficial in airway inflammation.

Recent studies suggest that NF-κB may also play a critical role in the pathogenesis of inflammatory bowel disease (IBD). Activated NF-κB is seen in colonic biopsy specimens from Chron's disease and ulcerative colitis patients (Ardite et al., 1998; Rogler et al., 1998; Schreiber et al., 1998). Activation is evident in the inflamed mucosa but not in uninflamed mucosa (Ardite et al., 1998; Rogler et al., 1998) and is associated with increased IL-8 mRNA expression in the same sites (Ardite et al., 1998). Furthermore, corticosteroid treatment strongly inhibits intestinal NF-κB activation and reduces colonic inflammation (Ardite et al., 1998; Schreiber et al., 1998). Again, inhibition of IL-8 production through the inhibition of NF-κB, as has been demonstrated by these compounds would be predicted be beneficial in inflammatory bowel disease.

Animal models of gastrointestinal inflammation provide further support for NF-κB as a key regulator of colonic inflammation. Increased NF-κB activity is observed in the lamina propria macrophages in 2,4,6,-trinitrobenzene sulfonic acid (TNBS)-induced colitis in mice with p65 being a major component of the activated complexes (Neurath et al., 1996; Neurath and Pettersson, 1997). Local administration of p65 antisense abrogates the signs of established colitis in the treated animals with no signs of toxicity (Neurath et al., 1996; Neurath and Pettersson, 1997). As such, one would predict that small molecule inhibitors of NF-κB would be useful in the treatment of IBD.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising human rheumatoid synovium (Handel et al., 1995; Marok et al., 1996; Sioud et al., 1998) and in animal models of the disease (Tsao et al., 1997). The staining is associated with type A synoviocytes and vascular endothelium (Marok et al., 1996). Furthermore, constitutive activation of NF-κB is seen in cultured synoviocytes (Roshak et al., 1996; Miyazawa et al., 1998) and in synovial cell cultures stimulated with IL-1 or TNFα (Roshak et al., 1996; Fujisawa et al., 1996; Roshak et al., 1997). Thus, the activation of NF-κB may underlie the increased cytokine production and leukocyte infiltration characteristic of inflamed synovium. The ability of these compounds to inhibit NF-κB and thereby inhibit the production of pro-inflammatory mediators (e.g. cytokines and prostanoids) by these cells would be predicted to yield benefit in rheumatoid arthritis.

Biological Assays

The compounds of this invention may be tested in one of several biological assays to determine the concentration of compound, which is required to have a given pharmacological effect.

NF-κB activity may also be measured in an electrophoretic mobility shift assay (EMSA) to assess the presence of NF-κB protein in the nucleus. The cells of interest are cultured to a density of $1 \times 10^6$/mL. The cells are harvested by centrifugation, washed in PBS without $Ca^{2+}$ and $Mg^{2+}$ and resuspended in PBS with $Ca^{2+}$ and $Mg^{2+}$ at $1 \times 10^7$ cells/mL. To examine the effect of compound on the activation of NF-κB, the cell suspensions are treated with various concentrations of drug or vehicle (DMSO, 0.1%) for 30 min. at 37° C. prior to stimulation with TNF-α (5.0 ng/mL) for an additional 15 min. Cellular and nuclear extracts are prepared follows. Briefly, at the end of the incubation period the cells ($1 \times 10^7$ cells) are washed 2× in PBS without $Ca^{2+}$ and $Mg^{2+}$. The resulting cell pellets are resuspended in 20 uL of Buffer A (10 mM Hepes (pH 7.9), 10 mM KCl, 1.5 mM $MgCl_2$, 0.5 mM dithiothreitol (DTT) and 0.1% NP-40) and incubated on ice for 10 min. The nuclei are pelleted by microcentrifugation at 3500 rpm for 10 min at 4° C. The resulting supernatant was collected as the cellular extract and the nuclear pellet was resuspended in 15 uL Buffer C (20 mM Hepes (pH 7.9), 0.42 M NaCl, 1.5 mM $MgCl_2$, 25% glycerol, 0.2 mM EDTA, 0.5 mM DTT, and 0.5 mM phenylmethylsulphonyl fluoride (PMSF)). The suspensions are mixed gently for 20 min at 4° C. then microcentrifuged at 14,000 rpm for 10 min at 4° C. The supernatant is collected and diluted to 60 uL with Buffer D (20 mM Hepes (pH 7.9), 50 mM KCl, 20% glycerol, 0.2 mM EDTA, 0.5 mM DTT, and 0.5 mM PMSF). All samples are stored at −80° C. until analyzed. The protein concentration of the extracts is determined according to the method of Bradford (Bradford, 1976) with BioRad reagents.

The effect of compounds on transcription factor activation is assessed in an electrophoretic mobility shift assay (EMSA) using nuclear extracts from treated cells as described above. The double stranded NF-κB consensus oligonucleotides (5'-AGTTGAGGGGACTTTCCCAGGC-3') are labelled with $T_4$ polynucleotide kinase and [g-$^{32}$P] ATP. The binding mixture (25 uL) contains 10 mM Hepes-NaOH (pH 7.9), 4 mM Tris-HCl (pH 7.9), 60 mM KCl, 1 mM EDTA, 1 mM dithiothreitol, 10% glycerol, 0.3 mg/mL bovine serum albumin, and 1 ug poly(dI-dC)opoly(dI-dC). The binding mixtures (10 ug nuclear extract protein) are incubated for 20 min at room temperature with 0.5 ng of $^{32}$P-labelled oligonucleotide (50,000-100,000 cpm) in the presence or absence of unlabeled competitor after which the mixture is loaded on a 4% polyacrylamide gel prepared in 1× Tris borate/EDTA and electrophoresed at 200 V for 2 h. Following electrophoresis the gels are dried and exposed to film for detection of the binding reaction.

The effect of compounds on the phosphorylation of IκB may be monitored in a Western blot. Cellular extracts are subjected to sodium dodecyl sulfate-polyacrylamide gel electrophoresis (SDS-PAGE) on 10% gels (BioRad, Hercules, Calif.) and the proteins transferred to nitrocellulose sheets (Hybond™-ECL, Amersham Corp., Arlington Heights, Ill.). Immunoblot assays are performed using a polyclonal rabbit antibody directed against IκBα or IκBβ followed with a peroxidase-conjugated donkey anti-rabbit secondary antibody (Amersham Corp., Arlington Heights, Ill.). Immunoreactive bands are detected using the Enchanced Chemiluminescence (ECL) assay system (Amersham Corp., Arlington Heights, Ill.).

Assays for IκB kinases were conducted as follows: IKK-α was expressed as a hexa-histidine tagged protein in baculovirus-infected insect cells and purified over a Ni-NTA affinity column. Kinase activity was assayed using 50 ng of purified protein in assay buffer (20 mM Hepes, pH 7.7, 2 mM $MgCl_2$, 1 mM $MnCl_2$, 10 mM β-glycerophosphate, 10 mM NaF, 10 mM PNPP, 0.3 mM $Na_3VO_4$, 1 mM benzamidine, 2 μM PMSF, 10 μg/ml aprotinin, 1 ug/mL leupeptin, 1 ug/mL pepstatin, 1 mM DTT) containing various concentrations of compound or DMSO vehicle and ATP as indicated (Pharmacia Biotech Inc., Piscataway, N.J.). The reaction was started by the addition of 200 ng IκB-GST (Santa Cruz Biotechnology, Inc., Santa Cruz, Calif.), in a total volume of 50 uL. The reaction was allowed to proceed for 1 h. at 30° C. after which the reaction was terminated by the addition of EDTA to a final concentration of 20 mM. Kinase activity was determined by dissociation-enhanced lanthanide fluorescence immunoassay (Wallac Oy, Turku, Finland) using a phospho-IκB-α (Ser32) antibody (New England Biolabs, Inc., Beverly, Mass.) and an $Eu^{3+}$-labelled anti-rabbit IgG (Wallac Oy, Turku, Finland). The plates were read in a VICTOR 1420 Multilabel Counter (Wallac), using a standard europium protocol (excitation 340 nm, emission 615 nm; fluorescence measured for 400 μs after a 400 usec delay). Data are expressed as fluorescence (cps) units.

IKK-β was expressed as a GST-tagged protein, and its activity was assessed in a 96-well scintillation proximity assay (SPA). Briefly, IKK-β was diluted in assay buffer as described above (20 nM final), with various concentrations of compound or DMSO vehicle, 240 nM ATP and 200 nCi [γ-$^{33}$P]-ATP (10 mCi/mL, 2000 Ci/mmol; NEN Life Science Products, Boston, Mass.). The reaction was started with the addition of a biotinylated peptide comprising amino acids 15-46 of IκB-α (American Peptide) to a final concentration of 2.4 μM, in a total volume of 50 uL. The sample incubated for one hour a 30° C., followed by the addition of 150 uL of stop buffer (PBS w/o $Ca^{2+}$, $Mg^{2+}$, 0.1% Triton X-100 (v/v), 10 mM EDTA) containing 0.2 mg streptavidin-coated SPA PVT beads (Amersham Pharmacia Biotech, Piscataway, N.J.). The sample was mixed, incubated for 10 min. at room temperature, centrifuged (1000×g, 2 minutes), and measured on a Hewlett-Packard TopCount.

In addition, IKK-β or IKK-α activity is measured by phosphorylation of recombinant GST-IkappaBalpha using time-resolved fluorescence resonance energy transfer (TR-FRET) in 384-well microtitre plates. Briefly IKK-βor IKK-α is diluted in assay buffer (50 mM HEPES pH 7.4 containing 10 mM magnesium chloride, 1 mM CHAPS, 1 mM DTT and 0.01% w/v BSA) to 5 nM final concentration. This is added to various concentrations of compound or DMSO vehicle and the reaction started by addition of 25 nM GST-IkappaBalpha and 1 μM ATP in assay buffer to a volume of 30 uL. After incubation for 30 min at ambient temperature the reaction was stopped by addition of 50 mM pH 7.4 EDTA (15 uL). Detection of phophorylated product was achieved by addition of a LANCE europium chelate labelled specific anti-phosphoserine monoclonal antibody at 0.5 nM final concentration (Cell signalling Technology via Perkin Elmer) and allophycocyanin labelled anti-GST antibody at 10 nM final concentration (Prozyme) to give a final volume of 60 μl. After a further incubation at ambient temperature of a least 30 min the signal was read on a Perkin Elmer Discovery fluorimeter.

The effect of IKK-β inhibitors on primary synovial fibroblast mediator production was assesses as follows: Primary cultures of human RSF were obtained by enzymatic digestion of synovium obtained from adult patients with rheumatoid arthritis as previously described (Roshak et al., 1996b). Cells were cultured in Earl's Minimal Essential Medium (EMEM) which contained 10% fetal bovine serum (FBS), 100 units/ml penicillin and 100 μg/ml streptomycin (GIBCO, Grand Island, N.Y.), at 37° C. and 5% $CO_2$. Cultures were used at passages 4 through 9 in order to obtain a more uniform type B fibroblast population. For some studies, fibroblasts were plated at $5\times10^4$ cells/mL in 16 mm (diameter) 24 well plates (Costar, Cambridge, Mass.). Cells (70-80% confluence) were exposed to IL-1β (1 ng/mL) (Genzyme, Cambridge, Mass.) for the designated time. Drugs in DMSO vehicle (1%) were added to the cell cultures 15 minutes prior to the addition of IL-1. Studies were conducted 3-4 times using synovial cells from different donors. RSF cellular extracts were prepared from cells treated as described above. Briefly, human RSF were removed by trypsin/EDTA, washed, and harvested by centrifugation. Cellular extracts were prepared as previously described (Dignarn et al., 1983; Osborn, et al., 1989). Briefly, at the end of the incubation period the cells ($1\times10^7$ cells) were washed 2× in PBS without $Ca^{2+}$ and $Mg^{2+}$. The resulting cell pellets were resuspended in 20 uL of Buffer A (10 mM Hepes (pH 7.9), 10 mM KCl, 1.5 mM MgCl$_2$, 0.5 mM.

Effect of IKK-β inhibition on human monocyte stimulated eicosanoid and cytokine production was assessed as follows: Monocytes were isolated from heparinized whole blood by double gradient centrifugation as previously described. Isolated monocyte enriched PBMCs were then adhered to 24 well culture plates at 2×10$^6$ cells/mL in RPMI 1640 10% FBS (Hyclone, Logan, Utah) for 2 h. to further enrich the monocyte population. The media was then removed, cells washed once with RPMI 1640, and 1 mL RPMI 1640 10% FBS was added to the wells. Test compounds are added to the wells with a final vehicle concentration of 0.05% DMSO. Monocytes were activated by the addition of 200 ng/mL endotoxin (LPS; $E.\ coli$ serotype 026:B6)(Sigma, St. Louis, Mo.) and incubated for 24 hrs. Cell-free supernates were analyzed by ELISA for TNF-α (EIA developed at SB), PGE$_2$ (Cayman Chemical, Ann Arbor, Mich.), and IL-8 and IL-6 Biosource International, Camarillo, Calif.). Viability of the cells was determined by trypan blue exclusion.

Effect of IKK-β inhibitors on phorbol ester-induced inflammation was assessed as follows: The inflammatory response induced by the cutaneous application of phorbol ester (PMA) to the external pinnae of Balb/c mice has proven to be a useful model to examine multifactorial inflammatory cell infiltration and inflammatory alteration of epidermis. The intense inflammatory lesion is dominated by neutrophil infiltration, which can be easily quantified by measurement tissue concentration myeloperoxidase, an azuriphilic granular enzyme present in neutrophils. In addition, the overall intensity of the inflammatory response can be measured by determination of ear thickness. Balb/c mice (n=6/group) were administered drug treatment or vehicle followed by PMA (4 ug/ear). The mice were sacrificed 4 h. later, the ear thickness determined and NF-κB activation was monitored by IκBα western or EMSA analysis.

Effect of IKK-β inhibitors on rat carrageenan-induced paw edema was assessed as follows: Male Lewis rats (Charles River, Raleigh, N.C.) were housed and allowed free access to food and water, and weighed between 200-275 g for each experiment. Compound or vehicle (0.5% Tragacanth (p.o.) or 10% DMSO, 5% DMA, 30% Cremophor (i.p.)) was administered 30 minutes to 1 hour prior to the carrageenan injection. Edema was induced by injection of 1% carrageenan in sterile dH2O (0.05 ml/paw) into the plantar surface of the right hindpaw. Paw thickness was measured prior to administration of compound or vehicle, and again at 3 hours, to determine change in paw volume. Rats were euthanized by CO2 inhalation and the right hindfoot was removed, immediately frozen in liquid nitrogen and stored at −80 C for analysis.

To determine the effects of an IKK-2 inhibitor in the mouse collagen-induced arthritis (CIA) model, 12 male DBA/1 mice (20-22 grams) per treatment group were immunized on day 0 with a total of 100 uL of complete Freund's adjuvant (CFA) containing 200 ug of bovine type II collagen. On day 21 mice were boosted with 100 uL of phosphate buffered saline (PBS) containing 200 ug of bovine type II collagen (the 100 uL of collagen/CFA or collagen/PBS was injected subcutaneously into the tail). The IKK-2 inhibitor in vehicle, or vehicle alone, was administered intraperitoneally, twice daily, from days 1 through 40 (disease symptoms are evident beginning on days 25-28). Two additional treatment groups included the positive control etanercept (Enbrel) (4 mg/kg, intraperitoneally, every other day), and the etanercept vehicle (PBS). Mice were scored daily, through day 50, for clinical symptoms (see below), and paw thicknesses were measured. In addition to the 12 mice per treatment group that were scored throughout the experiment, at several time points during the course of disease satellite mice (3-5 per treatment group) treated as described above were utilized to measure cytokine/chemokine levels and p65 levels in the paw, the ex vivo antigen recall response by draining lymph node antigen recall response by draining lymph node Induction of arthritis AIA is induced by a single injection of 0.75 mg of $Mycobacterium\ butyricum$ (Difco, Detroit, Mich.) suspended in paraffin oil into the base of the tail of male Lewis rats aged 6-8 weeks (160-180 g). Hindpaw volumes are measured by a water displacement method on day 16 and/or day 20. Test compounds were homogenized in a suitable vehicle and administered by a suitable route. Control animals are administered vehicles alone. Two dosing protocols are genrally used: prophylactic dosing, which is initiated on the day of adjuvant injection and therapeutic administration, initiated on day 10 once inflammation has been established.

Clinical Scoring

Each paw was assigned a score ranging from 0-4, based on the following criteria:
0=no inflammation
1=single swollen digit
2=several swollen digits, mild paw swelling
3=several swollen digits, moderate paw swelling
4=all digits swollen, severe paw swelling All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to formula (I) hereinbelow:
(1) herein below:

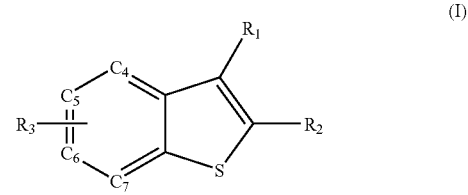

$R_1$ represents CONH$_2$;
$R_2$ represents NR$_4$R$_5$;
$R_3$ is selected from the group consisting of H, CN, CF$_3$, halogen, aryl, heteroaryl, alkyl, O-alkyl, and S-alkyl; and can be attached to either C$_4$, C$_5$, C$_6$ or C$_7$;
$R_4$ represents H or alkyl; and $R_5$ is selected from the group consisting of H, CO-alkyl, $SO_2$-alkyl, $CONH_2$, CONH-alkyl, CONH-aryl, CONH-heteroaryl, $CSNH_2$, CSNH-alkyl, CSNH-aryl, CSNH-heteroaryl, $SO_2NH_2$, $SO_2NH$-alkyl, $SO_2NH$-aryl, and $SO_2NH$-heteroaryl; or a pharmaceutically acceptable salt thereof.

2. A compound according to claim 1 wherein the compound is selected from the group consisting of:
- 2-Amino-6-(4-fluoro-phenyl)-benzo[b]thiophene-3-carboxylic acid amide; and
- 2-Ureido-benzo[b]thiophene-3-carboxylic acid amide.

* * * * *